United States Patent [19]

Pinza et al.

[11] Patent Number: 4,757,142
[45] Date of Patent: Jul. 12, 1988

[54] PROCESS FOR PREPARING 6-AMINO-3-HYDRAZINOPYRIDAZINE DERIVATIVES

[75] Inventors: Mario Pinza, Corsico; Riccardo Monguzzi, Monza; Riccardo Colombo, Sesto San Giovanni, all of Italy

[73] Assignee: ISF Societa Per Azioni, Milan, Italy

[21] Appl. No.: 862,723

[22] Filed: May 13, 1986

[30] Foreign Application Priority Data

May 13, 1985 [IT] Italy .............................. 20674 A/85

[51] Int. Cl.$^4$ .................. C07D 237/20; C07D 237/12
[52] U.S. Cl. ...................................... 544/224; 544/236
[58] Field of Search .................. 544/224; 560/24, 169; 546/306

[56] References Cited

U.S. PATENT DOCUMENTS 4,002,753  1/1977  Carpi et al. ........................ 544/224
4,575,552  3/1986  Farina et al. ........................ 544/224

FOREIGN PATENT DOCUMENTS 202095    11/1986  European Pat. Off. .
1470747   4/1977   United Kingdom .
2088376A  6/1982   United Kingdom ................ 544/224

OTHER PUBLICATIONS

Parravicini, F., et al., *Il Farmaco* (Ed. Sci) 34, 299–310 (1979).
Pifferi et al., *J. Med. Chem.*, 18, 7, 741–746 (1975).

Primary Examiner—Donald G. Daus
Assistant Examiner—E. Bernhardt
Attorney, Agent, or Firm—Nancy S. Mayer; Janice E. Williams; Alan D. Lourie

[57] ABSTRACT

A novel process for preparing 6-amino-3-hydrazinopyridazine derivatives comprising reacting a 3-amino-6-chloropyridazine derivative with ethyl carbazate under aqueous conditions.

8 Claims, No Drawings

PROCESS FOR PREPARING 6-AMINO-3-HYDRAZINOPYRIDAZINE DERIVATIVES

This invention relates to an improved process for preparing 6-amino-3-hydrazinopyridazine derivatives. Cadralazine has been described as being a useful antihypertensive agent. Specifically this invention relates to an improved process for preparing cadralazine.

In the literature cadralazine and related aminopyridazinylcarbazates have been prepared by reacting a 3-amino-6-chloropyridazine derivative with an alkyl carbazate. These reactions have generally been carried out using the free base of the 3-amino-6-chloropyridazine derivative and are generally characterised by the use of organic solvents or the use of molten reagents without a solvent, and the use of comparatively high temperatures and/or relatively long reaction times. It has also been recognised that these reaction conditions give rise to undesirable impurities.

The preparation of cadralazine(ethyl 2-[6-[ethyl-(2-hydroxypropyl)amino]-3 pyridazinyl]hydrazinecarboxylate) has been described in U.K. Pat. No. 1,470,747 where there is an indication (at page 2, line 20) that the reaction was preferably carried out at 140°–160° C. The specific example describes conditions in which the reagents are heated at 145° for one hour in the absence of a solvent. The preparation of cadralazine has also been described in Il Farmaco (Ed. Sci.) 34 299–310 (1979). Table 1 includes cadralazine as compound IIg and indicates that it was prepared in 25% yield by method A, that is the reactants were refluxed for 8 hours in amyl alcohol (b.p. 137° C.). At lines 7/8 on page 302 there is an indication that this process gives rise to side-reactions including the production of 2,3-dihydro-1,2,4-triazolo-[4,3-b]pyridazin-3-ones, e.g. compound A.

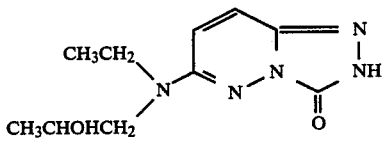

(A)

The preparation of some tertiary alkyl aminopyridazinylcarbazates is described in GB No. 2088376A (Gruppo Lepetit SpA). This specification states "the reaction is generally completed in 24–36 hours or more" and the specific Examples (at page 4 lines 22–31) describe a process in which the reactants are refluxed in 2-methoxyethanol (b.p. 124° C.) for 26 hours.

Surprisingly, we have discovered that cadralazine can be prepared under aqueous conditions (as opposed to using an organic solvent or molten reactants) and that this process can be carried out relatively quickly or at relatively low temperatures, and that such aqueous conditions give the product in higher yield and higher purity than known methods; in addition difficulties arising from transesterification of the carbazate group can be avoided.

According to the present invention we provide a process for the preparation of a compound of Structure (4), which comprises reacting a compound of Structure (3) with ethyl carbazate under aqueous conditions. Preferably this reaction is carried out under acidic conditions i.e. in a pH range of 0.1 to 5.0 preferably 0.5 to 3.0.

Preferably the reaction is carried out with the compound (3) being in the form of an addition salt with a mineral acid, such as hydrochloric, sulphuric or phosphoric acid, or with one equivalent of such an acid being added to the reaction mixture. It will be recognised that one mole of hydrochloric acid is generated in this reaction and that preferably an excess of ethyl carbazate is used in the reaction. Particularly preferably between 1.5 to 3.0 moles, especially 2.0 to 2.25 moles, of ethyl carbazate are used for each mole of the aminopyridazine (3).

Preferably this reaction is carried out at the boiling point of the aqueous mixture (about 100° C.). Whilst we have found that the reaction proceeds relatively quickly and is complete within about 6 hours we have found that there are no substantial disadvantages, e.g. generation of impurities, if the mixture is heated under reflux for up to 24 hours.

Whilst water-miscible organic solvents such as alcohols, e.g. ethanol, can be added to the reaction mixture there is no advantage in doing so and preferably the reaction is carried out in the absence of an organic cosolvent.

Preferably the reaction is carried out at a reasonable concentration, that is at least one mole of the aminopyridazine (3) per liter.

This process not only has the advantages that the use of organic solvents (and their expense and danger from flammability) can be avoided but it also has the advantage that the compound of Structure (3) can be used in the form of an acid addition salt rather than in the form of a free base. Particularly advantageously we have found that it is possible to use an acid addition salt of the compound of Structure (3) which has been prepared by fusing 3,6-dichloropyridazine (1) with the secondary amine without the need for isolation and purification of the salt of (3) or the free base (3). We have found that even if an excess of the secondary amine is used, for example even if more than a one molar excess is used, then it is not necessary to remove the unreacted amine before reacting the product with ethyl carbazate.

When the reaction steps are combined in a 'one-pot' process then preferably an excess of the amine (2) is used in the first step of the reaction, particularly preferably between 2.0 and 2.5 moles of the amine for each mole of 3,6-dichloropyridazine. Preferably the reaction is carried out in the absence of a solvent at a temperature of about 80°–120° C., particularly 90°–100° C. If an excess of the amine (2) is used then in the second stage of the reaction an amount of acid equivalent to the excess of the amine (2) is added i.e. sufficient acid to form the acid addition salt of the compound of Structure (3); thus if 1 mole of 3,6-dichloropyridazine is used with 3 moles of the amine (2) then preferably 2 molar equivalents of a mineral acid is added to the reaction mixture before the ethyl carbazate is added. Preferably the acid added is hydrochloric or sulphuric acid.

Scheme 1

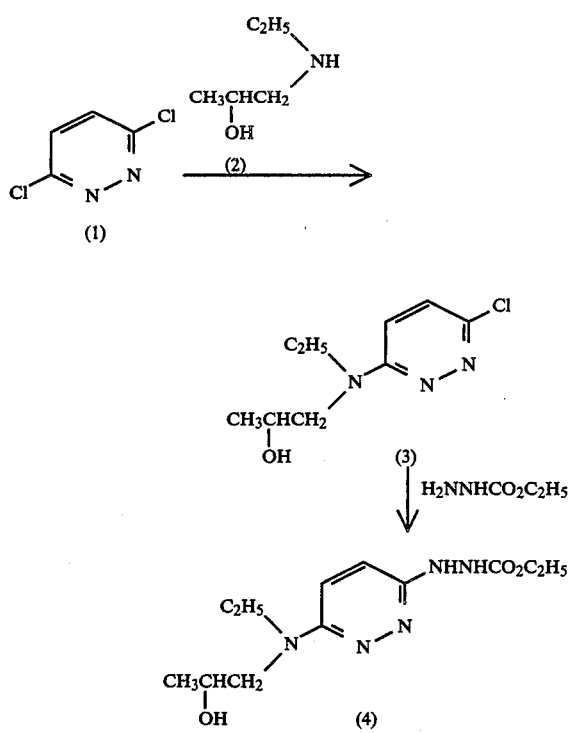

The invention is illustrated by the following Example in which temperatures are given in degrees Celsius:

EXAMPLE 1

Ethyl 2-[6-[ethyl-(2-hydroxypropyl)amino]-3-pyridazinyl]hydrazinecarboxylate (4) (cadralazine)

To 583 g (3.91 moles) of melted 3,6-dichloropyridazine (I) (at about 70°) was added under nitrogen and stirring over 6 h 1 liter (8.67 moles) of N-ethyl-N'-(2-hydroxypropyl)amine (2). The mixture was stirred at 95° for 16 h. After cooling to 40°, 1.5 liters of water, 470 ml of 37% (w/w) hydrochloric acid and 884 ml (8.49 moles) of ethyl hydrazinecarboxylate were added. The solution was refluxed under nitrogen for 20 h. After cooling to room temperature the mixture was brought to pH 8.5 with 32% (w/w) ammonium hydroxide. The mixture was maintained at 0° overnight, then filtered. The precipitate was washed with cold water until elimination of chloride ions. Crystallisation from ethanol 95% afforded 776 g (70%) of the title compound m.p. 165°.

What is claimed is:

1. A process for preparing a compound of Structure (4)

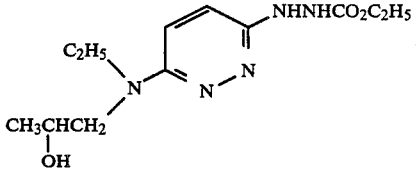

which comprises reacting a compound of Structure (3)

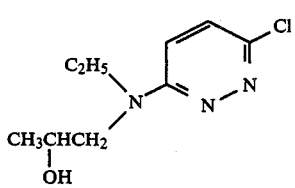

with ethyl carbazate, characterised in that the reaction is carried out in water and the compound of Structure (3) is in the form of the hydrochloride, sulfate, or phosphate salt.

2. A process according to claim 1 in which the reaction is carried out at a pH range of 0.1 to 5.0.

3. A process according to claim 1 in which the reaction is carried out at a pH range of 0.5 to 3.0.

4. A process according to claim 1 characterised in that the compound of Structure (3) is prepared by reacting 3,6-dichloropyridazine with the amine of Structure (2)

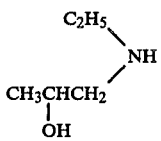

and without isolation of the product a sufficient amount of hydrochloric, sulfuric, or phosphoric acid is added to form the acid addition salt of the compound of Structure (3) which is then reacted with ethyl carbazate to give a compound of Structure (4)

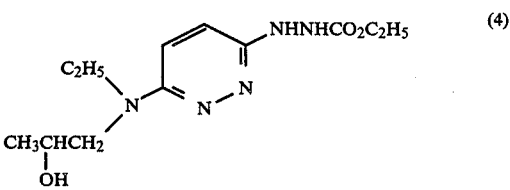

which is isolated by neutralizing the reaction mixture.

5. A process according to claim 1 in which from 1.5 to 3.0 moles of ethyl carbazate are used for each mole of the compound of Structure (3).

6. A process according to claim 1 in which the product of Structure (4) is isolated by adjustment to pH 8.5 with aqueous ammonia.

7. A process according to claim 4 or 5 in which in the preparation of a compound of Structure (3) from 2.0 to 2.5 mole of the amine of Structure (2) is used for each mole of 3,6-dichloropyridazine and the reaction is carried out in the absence of a solvent at a temperature between 80°-120° C.

8. A process according to any one of claims 1 to 6 in which the acid used is hydrochloric or sulphuric acid.

* * * * *